United States Patent [19]

Higuchi

[11] 3,968,245

[45] July 6, 1976

[54] SYMPATHOMIMETIC TOPICAL AND PERCUTANEOUS ADMINISTRATION WITH HALOGENATED PROMOTERS

[75] Inventor: Takeru Higuchi, Lawrence, Kans.

[73] Assignee: Alza Corporation, Palo Alto, Calif.

[22] Filed: May 1, 1975

[21] Appl. No.: 573,468

Related U.S. Application Data

[60] Division of Ser. No. 406,011, Oct. 12, 1973, Pat. No. 3,891,757, which is a continuation-in-part of Ser. No. 197,919, Nov. 11, 1971, Pat. No. 3,787,571.

[52] U.S. Cl. .................................. 424/330; 424/343
[51] Int. Cl.² .............. A61K 31/135; A61K 31/045; A61K 47/00
[58] Field of Search ........................... 424/330, 343

[56] References Cited
UNITED STATES PATENTS

| | | | |
|---|---|---|---|
| 3,787,571 | 1/1974 | Higuchi | 424/239 |
| 3,891,757 | 6/1975 | Higuchi | 424/310 |

OTHER PUBLICATIONS

Lehman et al. J. Pharmacol. 63:453–465 (1938) "Trichloroethanol, Tribromoethanol Chloral Hydrate and Bromal Hydrate."

Hewer et al. Lancet 235:129–1291 (1938) "Trichloroethanol as Basal Marcotic."

Case Anesthesiology 41:523–527 (1943) "The Present Status of Trichloroethanol."

Primary Examiner—Shep K. Rose
Attorney, Agent, or Firm—Paul L. Sabatine

[57] ABSTRACT

Dermal compositions are disclosed with comprise trichloroethanol or trifluoroethanol as one component of a vehicle having solubilized therein a drug or other beneficial chemical compound. Also disclosed is a method for administering a drug or other beneficial chemical compound to the body which comprises contacting the skin with the drug or compound in the presence of trichloroethanol or trifluoroethanol which acts as an absorption promoter to enhance the topical or percutaneous absorption of the active drug or compound.

6 Claims, No Drawings

SYMPATHOMIMETIC TOPICAL AND PERCUTANEOUS ADMINISTRATION WITH HALOGENATED PROMOTERS

CROSS-REFERENCE TO RELATED APPLICATIONS

This application is a division of copending U.S. patent application Ser. No. 406,011 filed on Oct. 12, 1973 and now U.S. Pat. No. 3,891,757, which application is a continuation-in-part of U.S. patent application Ser. No. 197,919 filed on Nov. 11, 1971, now U.S. Pat. No. 3,787,571, issued on Jan. 22, 1974 and assigned to the same assignee of this invention, and benefit of their filling dates is claimed in this application.

BACKGROUND OF THE INVENTION

This invention relates to a composition and to a method for administering a drug or other beneficial chemical compound topically to the body. More especially, the invention concerns composition and a method for enhancing dermatological or percutaneous absorption of such active agents in compositions for the use of humans and domestic animals.

It is well known that the outer or surface division of the epidermis, known as the stratum corneum or horny layer of the skin, acts as a barrier to penetration of external substances into the immediate area as well as into the body. Often times, however, it is desired to increase the degree of dermatological or percutaneous absorption or penetration of a particular therapeutically active dermal preparation, as for example in the treatment of skin disorders, subcutaneous infections, cosmetic effects, or the like.

In this regard, several reagents and methods for increasing the permeability of the skin have been disclosed in the art. For example, occlusion of the skin with metal guards, plastics, or other wraps has been employed to increase the penetration of various agents into the epidermis. Similarly, an increased rate of absorption into the skin has been produced by adjusting the temperature of the skin and/or by regulating the temperature and relative humidity of the adjacent atmosphere. Most effective, however, have been the recent efforts directed toward the discovery and application of chemical absorption promoters which are employed as integral components of therapeutically active or bioaffecting compositions. Workers in this area have experienced varying degrees of success in their endeavors to locate truly effective topical or percutaneous absorption promoters, since a great number of chemical compounds have been found to promote absorption, at least to a degree, as for example in British Pat. No. 1,001,949 and U.S. Pat. No. 3,472,931.

SUMMARY OF THE INVENTION

Accordingly, it is an object of this invention to provide an improved means and method for promoting topical and percutaneous absorption of drugs, cosmetics, and other beneficial chemical compounds administered to humans and domestic animals in the form of topically applied compositions.

Another object of this invention is to provide improved topically active therapeutic and bio-affecting preparations which exhibit increased absorption into or through the skin.

In attaining the objects of this invention, one feature resides in compositions containing compounds for and to a method for increasing topical or percutaneous absorption of drugs, cosmetics and other beneficial chemical compounds which comprises contacting the skin with a drug, cosmetic or chemical compound in the presence of a vehicle having as one component thereof an absorption promoter consisting of either trichloroethanol (TCE) or trifluoroethanol (TFE). The absorption promoters of the invention can be used as the sole promoter and solubilizing agent for the drug, cosmetic or chemical compound, or they can be employed together with any additional pharmaceutically acceptable solvents, vehicles, bases, surface active agents, emulsifiers, and the like.

Other objects, features, and advantages of this invention will become more apparent from the following description.

DETAILED DESCRIPTION OF THE INVENTION

Percutaneous absorption refers to the passage of a substance from the surface of the skin through the horny layer of the epidermis, into the cellular epidermis and from there into the corium or dermis. Penetration of the substance through the horny layer constitutes percutaneous absorption for the purposes of this invention. The passage of the substance on into the corium and into the systemic circulation is considered to be the effect, or continuing result of percutaneous absorption. Once a chemical substance passes through the horny layer of the epidermis, there readily occurs further absorption or penetration through the stratum granulosum, stratum malpighii and stratum germinativum, on into the first connective tissue beneath the epidermis, and thence into the remainder of the body, since below the cellular layer referred to as stratum corneum there is very little resistance to penetration or absorption. Absorption into the horny layer alone, or further into the epidermis, without significant system absorption is considered to be topical absorption, and it is also referred to as retention.

In nature, when a penetratable substance is applied to the skin, an extremely small percentage of the substance is absorbed into the horny layer and retained there. An even smaller percentage of the substance absorbed into the horny layer passes therethrough into the underlying layers identified above, and thence into the systemic circulation of the human or animal. Thus, there is some degree of both natural retention and percutaneous absorption.

The present invention provides a process whereby this natural rate of percutaneous absorption and retention, and the amount of penetratable substance actually absorbed or retained are markedly increased. These effects are accomplished by contacting the skin with trichloroethanol or trifluoroethanol and simultaneously or in the presence thereof with the preferred drug, cosmetic or beneficial agent.

The substances referred to herein as stable, topically active compounds are drugs or other beneficial chemical compounds which can be applied topically to the skin for the purpose of beautifying surface conditions, medicating surface conditions or diseases, sub-surface diseases, or systemic disturbances, or creating skin conditions helpful in alleviating harmful or annoying external factors. Thus, topically active compounds include those eliciting a pharmacological or physiological response either at or near the site of application, as well as at a site remote therefrom. Drugs, cosmetics and compounds utilized according to this invention possess the ability to be solubilized or minutely dispersed in trichloroethanol, or trifluoroethanol or in a mixture thereof, thus forming a formulation for administering to the skin for percutaneous absorption or retention of the administered drug, cosmetic or compound. By the terms solubilize or dispersing is meant that the drug, cosmetic or chemical compound used herein is dissolved or held in suspension by normal mixing or shaking operations in trichloroethanol, or trifluoroethanol, or a mixture thereof, to the extent of at least about 0.01% by weight to about 30% by weight of the drug, cosmetic or compound in the promoter of choice.

Generally speaking, many drugs are useful in treating surface, sub-surface and systemic conditions by topical application, and the same can be made more effective if their percutaneous absorption rate or retention rate is increased such that preferred concentrations thereof will penetrate through the horny layer of the skin, or be retained therein, or both. Any of the standard drugs, cosmetics or the like used to treat the body or skin can be applied to the skin in the presence of the absorption promoters of this invention. "Drug" is used herein in its broadest sense as including any composition or substance that will produce a pharmacologic or physiologic response.

Suitable drugs for use in therapy with the absorption promoters of the invention include without limitation:

1. Protein drugs such as insulin;
2. Desensitizing agents such as ragweed pollen antigens, hay fever pollen antigens, dust antigen and milk antigen;
3. Vaccines such as smallpox, yellow fever, distemper, hog cholera, fowl pox, antivenom, scarlet fever, diphtheria toxoid, tetanus toxoid, pigeon pox, whooping cough, influenza, rabies, mumps, measles, poliomyelitis, Newcastle disease, etc.;
4. Anti-infectives, such as antibiotics, including penicillin, tetracycline, chlortetracycline, bacitracin, nystatin, streptomycin, neomycin, polymyxin, gramicidin, oxytetracycline, chloramphenicol, and erythromycin; sulfonamides, including sulfacetamide, sulfamethizole, sulfamethazine, sulfadiazine, sulfamerazine, and sulfisoxazole; anti-virals including idoxuridine; and other anti-infectives including nitrofurazone and sodium propionate; hexachlorophene, cetyl pyridinium chloride, pyrithione and its salts, undecylenic acid, and others;
5. Anti-allergenics such as antazoline, methapyrilene, chlorpheniramine, pyrilamine and prophenpyridamine;
6. Anti-inflammatories such as hydrocortisone, cortisone, hydrocortisone acetate, dexamethasone, dexamethasone 21-phosphate, fluocinolone, triamcinolone, medrysone, prednisolone, prednisolone 21-phosphate, and prednisolone acetate;
7. Decongestants such as phenylephrine, naphazoline, oxymetazoline and tetrahydrazoline;
8. Miotics and anticholinesterases such as pilocarpine, eserine salicylate, carbachol, di-isopropyl fluorophosphate, phospholine iodide, and demecarium bromide;
9. Mydriatics such as atropine sulfate, cyclopentolate, homatropine, scopolamine, tropicamide, eucatropine, and hydroxyamphetamine;
10. Sympathomimetics such as epinephrine, ophedrine, phenylephrine;
11. Sedatives and hypnotics such as pentobarbital sodium, phenobarbital, secobarbital sodium, codeine, ($\alpha$-bromoisovaleryl) urea, carbromal;
12. Psychic energizers such as 3-(2-aminopropyl) indole acetate and 3-(2-aminobutyl) indole acetate;
13. Tranquilizers such as reserpine, chlorpromazline, and thiopropazate;
14. Androgenic steroids such as methyltestosterone and fluoxymesterone;
15. Estrogens such as estrone, 17-estradiol, ethinyl estradiol, and diethyl stilbesterol;
16. Progestational agents such as progesterone, megestrol, melengestrol, chlormadinone, ethisterone, norethynodrel, 19-nor-progesterone, norethindrone, medroxyprogesterone and 17 $\alpha$-hydroxy-progesterone;
17. Humoral agents such as the prostaglandins, for example $PGE_1$, $PGE_2$, and $PGF_2\ \alpha$.
18. Antipyretics such as aspirin, sodium salicylate, and salicylamide;
19. Antispasmodics such as atropine, methantheline, papaverine, and methscopolamine bromide;
20. Anti-malarials such as the 4-aminoquinolines, 8-aminoquinolines, chloroquine, and pyrimethamine;
21. Antihistamines such as diphenhydramine, dimenhydrinate, tripelennamine, perphenazine, and chlorophenazine;
22. Cardioactive agents such as hydroflumethiazide, flumethiazide, chlorothiazide, and triamterene;
23. Nutritional agents such as vitamins, minerals and other compounds, essential amino acids and essential fats.
24. Anhidrotic agents such as atropine, aluminum, zinc, zirconium, and other metal salts and complexes;
25. Odorizing, deodorizing, or odor preventing agents, such as perfumes, aromatic oils, metal salts and complexes, and the like;
26. Antipruritic such as benzocaine, lidocaine, phenol, menthol, etc;
27. Antieczemic drugs such as metallic oxides, salts such as zinc oxide, sulfur and sulfur containing compounds such as sodium thiosulfate and thioglycollic acid, phenol and other phenolics, inorganic and organic mercurials, coal tars, etc.;
28. Agents that improve or effect the peeling, sloughing, keratinization or follicular character of the skin such as salicylic acid, resorcinol, phenol, sulfur, retinoic acid, benzoyl peroxide, thioglycollic acid, their derivatives and the like;
29. Other drugs having the same or different physiological activity as those recited above can be employed together with the absorption promoters within the slope of the present invention. Suitable mixtures of drugs can, of course, be dispensed with equal facility as with single component systems.

Drugs can be in various forms, such as uncharged molecules, components of molecular complexes, or nonirritating, pharmacologically acceptable salts such as hydrochloride, hydrobromide, sulphate, phosphate, nitrate, borate, acetate, maleate, tartrate, salicylate, etc. For acidic drugs, salts of metals, amines, or organic cations (e.g., quaternary ammonium) can be employed. Furthermore, simple derivatives of the drugs such as ethers, esters, amides, etc. which have desirable percutaneous absorption or retention producing characteristics but which are easily hydrolyzed by body pH, enzymes, etc., can be employed. Other beneficial chemical compounds may likewise be administered in the presence of the instant, non-toxic absorption promoters for the purpose of enhancing their absorption into or through the skin. Thus, for example, cosmetic agents, moisturizers, skin enrichment and toning agents, coloring and pigmenting agents, bleaching agents, sun screens, pigments and like compounds which are desirably applied topically to the skin may advantageously be combined with the promoters of this invention.

Another application of the present invention resides in patch testing which is becoming one of the most widely used methods for testing the skin to determine and identify sensitization and/or irritation potential to various substances such as drugs, cosmetics, and the like. The patch test consists of the application to uninjured skin, contiguous to the involved area, of substances suspected to be causes of the sensitivity and/or the irritation reaction. This is done by saturating the patch, a small piece of gauze, with one of these substances, occlusive, or semi-occlusive agents, in a concentration that will not cause irritation in the average person. The patch is then covered by a piece of impermeable protective material, such as cellophane, or like polymer, and applied to the skin by adhesive plaster. Unless there is pronounced irritation, the duration of a given test is typically about 36 to 72 hours after which the patch is removed. It can, however, be two to four days, or longer, before a positive reaction is observed in the tested area. By using the absorption promoters of this invention, a suspected chemical may be applied to the skin, left untouched for only so short a period of time necessary for absorption, whereupon the test will be complete without the necessity of the patient tolerating gauze pads, etc., over an extended period of time.

Both trichloroethanol and trifluoroethanol display a very strong proton donating propensity, and as such, these two compounds singly, or mixtures thereof, are especially suited to promote the absorption of hydrogen-accepting substances, such as amines, certain ketones, etc., as exemplified by the atropine, griseofulvin, diphenhydramine and the like. This result apparently is achieved by the ability of TCE and TFE to reduce the hydrogen binding tendency of the penetrating drug molecules, and/or the skin and tissues being penetrated. The two promoters also are well adapted for use in conjunction with hydrogen-donating substances such as phenols, prostaglandins, alcohols, salicylic acid, acetaminophen, chloramphenicol and the like. The enhanced degree of absorption in this instance is believed to result from masking of the fixed hydrogen-donating sites in the dermal tissue by the trichloroethanol and trifluoroethanol.

The incorporation of emollients such as lanolin and lanolin alcohols and their ethoxylated and/or acetylated products, glycerol, glycols and their derivatives, fatty acids, their esters, their alcohols and their derivatives, into the compositions of the present invention increase their percutaneous absorption and retention resulting effects, and also result in improved softening and moisturizing effects.

The absorption promoters can be used as the sole promoter and/or solubilizing agent for the drug, cosmetic or compounds destined for dermal application. Alternatively, the absorption promoters can constitute only one component of the preparations. Additional components include other pharmaceutically acceptable solvents, vehicles, or bases, as well as pharmaceutically acceptable surface active agents, emulsifiers, etc. The present absorption promoters can comprise one component of other pharmaceutical preparations such as lotions, creams, solutions and the like. Similarly, non-liquid preparations, such as jellies can be prepared by adding a thickener, e.g., silica, or an unguent base to prepared liquid preparations. The absorption delaying effect of these additives may be utilized in preparation of compositions wherein it is desirable to control the rate of absorption.

The present preparations can contain small amounts, for example 0.01% by weight or volume/volume or large amounts of trichloroethanol or trifluoroethanol, that is up to 99.99% by weight or volume/volume to promote percutaneous absorption or drug retention. However, it is generally preferred that preparations contain a higher percentage of absorption promoters than the active ingredient. Thus, the preparations according to this invention usually contain from about 50% of the absorption promoter, and about 0.01 to 30% of the drug. While the presence of even minute amounts of trichloroethanol and trifluoroethanol will enhance the absorption, it is readily apparent that their desired effect will be substantially diluted, and that the preferred ratio between pharmaceutically active ingredient and absorption promoter will be dictated by the recommended dosage of the active ingredient and the desired rate of application thereof.

The rate of absorption for the promoter can be measured by various known techniques. One technique is the radioactive technique. The use of radioactive substances has simplified the measurement problems allowing for more accurate determinations. Labeled compounds containing radioactive carbon atoms have been utilized to determine the rate and degree of percutaneous absorption as well as retention in the horny layer. Another method of estimating absorption is to utilize the biological activity exhibited by the compound. In this manner, the degree of absorption of applied glucocorticosteroids has been determined by studying vasoconstriction and blanching of the skin caused when these substances reach the corium. Another example of the utilization of biological activity to determine percutaneous absorption is the measurement of sweat secretion after application of anticholinergics.

In testing, particularly for the degree of the factor relied upon to determine penetration is the chemical substance which is absorbed rather than a factor inherent in the vehicle or absorption medium. Thus, both in vitro and in vivo tests have been devised for determining percutaneous absorption and retention. The general method utilized in the examples which follow for determining percutaneous absorption by the in vitro method is set out in U.S. Pat. No. 3,472,931.

Skin of normal appearance is removed from surgically amputated legs or breasts and immediately or after a period of refrigeration, cut into sections, wrapped in air-tight containers, and placed in a freezer at about −17°C to about −22°C for future use. Under the usual test conditions, at least four specimens are used in these experiments. The skin is handled as gently as possible to prevent cellular damage, and on removal from the freezer, thawing is carried out at room temperature for about one hour. The subcutaneous tissue or fat is cut from the under surface until the net-like pattern of the dermis is seen, with care taken to avoid cutting into the corium. Then, the skin is draped with the epidermis outward, over the mouth of an open glass well which is about 4 cm. in diameter, and secured in place by an elastic band. A plastic cylinder is then attached to the epidermis with a standard adhesive. Next, the glass well is connected to a second glass well by a glass tube. The second glass well contains a stopper so that the wells can be filled with physiological saline that bathes the corium side of the skin. The test solution or suspension containing the chemical compound, labled with a radioactive carbon atom is then applied to the epidermis contained within the small plastic cylinder. After given intervals, about 4 hours, 8 hours, 16 hours, 24 hours or larger, aliquots are removed from the glass well and measured for radioactivity. The amount of the radioactive substance which has penetrated is then determined, as measured in a Nuclear-Chicago Co. scintillation counter. Radioactivity is expressed as the number of counts per minute registered on the apparatus at a constant efficiency. The percent of applied counts per minute penetration in 24 hours is determined by dividing the total number of counts per minute recovered in 24 hours by the counts per minute applied, then multiplying by 100. The concentration in the saline and the corium is assumed to be the same and the volume added by the corium to be negligible.

The technique then is briefly to apply radioactive labeled material to the epidermal side, incubate in a temperature and humidity controlled chamber for about 4 to 24 hours and take samples of the saline bathing the corium to determine radioactivity in a scintillation counter. Thus, the percentage of applied material which has penetrated to the saline can be measured at any given time. The in vitro technique is modified to determine retention in the horny layer as follows. Similar skin is placed between two aluminum sheets and clamps are applied. This apparatus is immersed in water at about 60°C for about 2 minutes, the metal plates are removed from the skin, and the epidermis with stratum corneum is carefully removed from the dermis in a continuous sheet.

After the epidermis with stratum corneum is dried on a metal gauze, squares about 1 × 1 cm are cut from the tissue, and placed on glass slides at about 32°C and about 50% humidity. About 0.005 ml each of solutions of suspensions containing the chemical compound labeled with radioactive carbon atom in TCE, and other vehicles, such as ethanol and benzene, is placed on the stratum corneum side of the 1 cm² pieces and allowed to remain for 22 hours at about 22°C and about 50% humidity before washing. A group of four squares is usually treated with each solvent. After 22 hours the squares are individually washed for ten minutes in each of three washing fluids: (1) water with detergent, (2) 70% ethanol, and (3) benzene. The fluids are constantly stirred during the washing process. Following the washing, the squares of tissue are individually dissolved in 0.5 ml of methylbenzethonium chloride, scintillation fluid was added and the radioactivity counted.

An in vivo technique, described in U.S. Pat. No. 3,472,931, for determining percutaneous absorption utilizing the biological activity of the compounds is as follows: Healthy, young, adult male and/or female subjects are selected. The volar surfaces of the forearms are used and solutions or suspensions of corticosteroid compounds are prepared with 95% ethanol and TFE in dilutions ranging from about 1:100 to about 1:5,000,000. Then 0.02 ml of the various dilutions are applied from a dropping pipette on the flexor aspects of both forearms, slightly spread over an area of about 1 inch diameter and allowed to dry. The areas are left undisturbed for about 16 hours, and any sites of vasoconstriction are then noted. The TFE containing fluid was compared with the non-TFE containing fluid by placing each on equivalent areas of the forearms. The presence or absence of the physiologic reaction, i.e., vasoconstriction, was determined after a designated interval of time, and if the reaction was present, it was recorded as a positive response. This test can be utilized with corticosteroids as they cause blanching and vasoconstriction upon reaching the corium. Anti-cholinergics also are tested with this procedure by recording the presence or absence of the physiologic reaction, for example, the inhibition of sweating.

The in vivo technique used to determine retention in the horny layer involves a similar method where a solution containing the compound labeled with a radioactive carbon atom is applied to the body of animals or the forearms of human volunteers. The compound is solubilized in TCE and ethanol and in a placebo cream base. A 0.01 cc aliquot of each is applied to the forearm, about 10mg of the placebo cream base, and it is allowed to remain in place for about 60 minutes. The forearms are then washed with soap and water and wiped with wet ethanol sponges.

Surface counts were measured before and after washing procedures with the gas flow, thin Mylar window, skin probe made by the Nuclear Chicago Co. similar to that described in Malkinson, P.D.: Studies on the Percutaneous Absorption of C-14 Labeled Steroids by Use of the Gas Flow Cell, J. Invest. Derm. 31;19 (1958). The skin probe had a background count close to 30 counts per minute and operating at about 10% efficiency. Calculations to determine the amount of retention are made in the same manner as discussed concerning the in vitro method.

The effect of the promoters upon the rate of percutaneous absorption or retention begins to take place almost immediately upon application of the promotor to the skin, and, the following examples are illustrative of various formulations comprising the promoters for applying drugs, etc. to the skin.

EXAMPLE 1

A steroid solution containing 0.01 to 1000 mg of an estrogen component, 0.01 to 10,000 mg of a progestational component, 17.0 v/v of glycerine, 41 v/v trichloroethanol, $CCl_3CH_2OH$, lavender odor 0.05 v/v and distilled water, q.s. to 100 ml. The steroid components are mixed into the trichloroethanol in which previously the lavender had been dissolved. Next, the glycerine is added with stirring and distilled water added to volume.

EXAMPLE 2

Following the procedure of example 1, a steroid solution is prepared comprising 10 mg of ethynyl estradiol3-methyl ether 200 mg of 6-chloro-6-dehydro-17α-acetoxyprogesterone, 17 v/v of glycerine, 41 v/v of trichloroethanol, 0.05 v/v of lavender odor, and distilled water to 100 ml, with the mixing of the ingredients as in the example.

EXAMPLE 3

A topical solution comprising 10 mg of ethynyl estradiol-3-methyl ether and 500 mg of 6α-methyl-17α-acetoxyprogesterone are dissolved in turn in a portion of trichloroethanol and then sufficient trichloroethanol is added to produce the desired amount of solution, for example qs to 100 ml.

EXAMPLE 4

An aerosol liquid spray comprising 10 mg ethynyl estradiol-3-methyl ether, 200 mg of 6-chloro-6-dehydro-17α-acetoxyprogesterone, 10% trichloroethanol, and 89.8% of the propellants trichlorofluoromethane and dichlorodifluoromethane 50/50 is prepared by compound of the above ingredients and then placing it in an aerosol container.

EXAMPLE 5

Repeating the procedure of Example 4, except that the promoter trifluoroethanol ($CF_3CH_2OH$) is used for the promoter of Example 4, there is prepared a liquid, aerosol spray formulation.

EXAMPLE 6 from A sympathomimetic solution
containing 0.01 to 2500 mg of a sympathomimetic component selected from the group consisting of amphetamine 135.21, amphetamine sulfate 368.50, benzphetamine hydrochloride 275.82, cyclopentamine hydrochloride 177.72, dextroamphetamine hydrochloride 233.21, diethylpropion hydrochloride 241.76, ephedrine 174.24, ephedrine hydrochloride 201.70, epinephrine 183,21, epinephrine bitartrate 330.30, hydroxyamphetamine hydrobromide 232.12, isoproterenol sulfate 556.63, isosupine hydrochloride 337.85, methamphetamine hydrochloride 185.70, methoxamine hydrochloride 247,72, phenylephnine hydrochloride 203.67, and the like is prepared by repeating the procedure of Example 1 by using the sympathomimetic drug having a molecular weight of 130 to 560 in place of the steroid to prepare a topical and percutaneous drug solution.

EXAMPLE 7

A local anesthetic solution containing 0.01 to 2500 mg of a local anesthetic component selected from the group consisting of benzocaine 165.19, butethamine hydrochloride 272.78, butyl aminobenzoate 193.25, chloroprocaine hydrochloride 307.22, dibucaine 343.47, dibucaine hydrochloride 379.93, dimethisoquin hydrochloride 308.87, lidocaine 234,34, mepivacaine hydrochloride 282.82, phenacaine hydrochloride 334.85, procaine hydrochloride 272.78, tetracaine hydrochloride 300.83 and the like is prepared by repeating the procedure of Example 1 and using the anesthetic having a molecular weight range of 150 to 500 in lieu of the steroid to prepare a topical and percutaneous drug solution.

This invention provides a means and improved method for enhancing the percutaneous absorption of drugs and other beneficial chemical compounds, and it is suitable for employment in conjunction with drugs which are either hydrogen-accepting or hydrogen-donating. While there have been shown and described and pointed out the fundamental novel features of the invention as applied to the preferred embodiments, those skilled in the art will appreciate that various modifications, changes and omissions in the method for enhancing the percutaneous absorption of drugs illustrated and described can be made without departing from the spirit of the invention. It is the intention, therefore, to be limited only by the scope of the following claims:

What is claimed is:

1. A pharmaceutical composition of matter comprising a first ingredient selected from the group of pharmaceutically acceptable topical and percutaneous absorption promoters consisting of trichloroethanol, trifluoroethanol and mixtures thereof, and about 0.01 to 30% of at least one local, topically administered sympathomimetic drug as a second ingredient, and wherein when topically administered, the first ingredient is a promoter for increasing topical retention and percutaneous absorption of a therapeutically effective amount of the second sympathomimetic ingredient.

2. The pharmaceutical composition of matter according to claim 1 wherein the sympathomimetic drug is a member selected from the group consisting of amphetamine, amphetamine sulfate, benzphetamine hydrochloride, cyclopentamine hydrochloride, dextroamphetamine hydrochloride, diethylpropion hydrochloride, ephedrine, ephedrine hydrochloride, epinephrine, epinephrine bitartrate, hydroxyamphetamine hydrobromide, isoproternol sulfate, isosupine hydrochloride, methamphetamine hydrochloride, methoxyamine hydrochloride, and phenylephrine hydrochloride.

3. The pharmaceutical composition of matter according to claim 1 wherein the sympathomimetic drug has a molecular weight of 130 to 560.

4. In a method for producing a local, topical sympathomimetic effect, the improvement consisting in the step of administering cutaneously a pharmaceutical composition consisting of a first ingredient selected from the group of topical absorption promoters consisting of trichloroethanol, trifluoroethanol and mixtures thereof, and a second ingredient consisting of about 0.01 to 30% by weight of a sympathomimetic drug selected from the group consisting of amphetamine, benzphetamine, cyclopentamine, dextroamphetamine, diethylpropion, ephedrine, epinephrine, hydroxyamphetamine, isoproterenol, isosupine, methamphetamine, methoxamine, and pehnylephrine, and wherein the first ingredient is an absorption promoter for increasing the retention and percutaneous absorption of a therapeutically effective amount of the second ingredient during the topical administration thereof.

5. In a method for producing a local sympathomimetic effect according to claim 4 wherein the pharmaceutical composition contains 0.01 to 99.99% of the first ingredient and from 0.01 to 30% of the second ingredient.

6. In a method for producing a local sympathomimetic effect according to claim 4 wherein the pharmaceutical composition contains a pharmaceutically acceptable carrier.

* * * * *